US012290637B2

(12) United States Patent
MacLoughlin et al.

(10) Patent No.: US 12,290,637 B2
(45) Date of Patent: *May 6, 2025

(54) GAS THERAPY SYSTEM FOR DELIVERY OF MEDICAMENT

(71) Applicant: STAMFORD DEVICES LIMITED, Dangan (IE)

(72) Inventors: Ronan MacLoughlin, Craughwell (IE); Shaun Porter, Rosscahill (IE); Conor Duffy, Roscahill (IE); John Power, Moycullen (IE)

(73) Assignee: STAMFORD DEVICES LIMITED, Galway (IE)

( * ) Notice: Subject to any disclaimer, the term of this patent is extended or adjusted under 35 U.S.C. 154(b) by 176 days.

This patent is subject to a terminal disclaimer.

(21) Appl. No.: 18/061,564

(22) Filed: Dec. 5, 2022

(65) Prior Publication Data

US 2023/0133932 A1 May 4, 2023

Related U.S. Application Data

(63) Continuation of application No. 16/621,560, filed as application No. PCT/EP2018/067937 on Jul. 3, 2018, now Pat. No. 11,534,570.

(30) Foreign Application Priority Data

Jul. 4, 2017 (EP) .................................... 17179658

(51) Int. Cl.
*A61M 16/14* (2006.01)
*A61M 11/00* (2006.01)
(Continued)

(52) U.S. Cl.
CPC ............ *A61M 16/14* (2013.01); *A61M 11/00* (2013.01); *A61M 16/0069* (2014.02);
(Continued)

(58) Field of Classification Search
CPC .............. A61M 16/00; A61M 16/0003; A61M 16/0057; A61M 16/0066; A61M 16/0069;
(Continued)

(56) References Cited

U.S. PATENT DOCUMENTS 6,216,690 B1 * 4/2001 Keitel ................ A61M 16/026 128/204.21
11,534,570 B2 * 12/2022 MacLoughlin ....... A61M 16/14
(Continued)

FOREIGN PATENT DOCUMENTS

WO 2007/008825 A2 1/2007
WO 2007/008825 A3 1/2007
(Continued)

OTHER PUBLICATIONS

International Search Report mailed Sep. 18, 2018 in International Application No. PCT/EP2018/067937 (5 pages).
Written Opinion of the International Searching Authority mailed Sep. 18, 2018 in International Application No. PCT/EP2018/067937 (8 pages).

*Primary Examiner* — Joseph D. Boecker
(74) *Attorney, Agent, or Firm* — Bookoff McAndrews, PLLC

(57) ABSTRACT

A gas therapy system (1) has a flow line (3, 2), a coupler (6) to a gas source, and an aerosol generator (4) for aerosol delivery, and a patient interface such as a nasal interface (2). A controller (10) is configured to modulate gas flow and aerosol delivery in real time. The controller changes gas flow rate and dynamically reduces aerosol delivery during upper gas flow rates such as 60 LPM, and activates aerosol delivery during lower gas flow rates of for example 10 LPM. The control may also include sensors to detect breathing, so that there is a bias towards increased aerosol delivery during inhalation in addition to during lower level gas flow.

20 Claims, 7 Drawing Sheets

(51) Int. Cl.
  *A61M 11/02* (2006.01)
  *A61M 16/00* (2006.01)
  *A61M 16/06* (2006.01)
  *A61M 16/16* (2006.01)

(52) U.S. Cl.
  CPC ...... *A61M 16/026* (2017.08); *A61M 16/0666* (2013.01); *A61M 11/005* (2013.01); *A61M 11/02* (2013.01); *A61M 2016/0018* (2013.01); *A61M 2016/0027* (2013.01); *A61M 16/0672* (2014.02); *A61M 16/16* (2013.01); *A61M 16/161* (2014.02); *A61M 2202/0208* (2013.01); *A61M 2205/3317* (2013.01); *A61M 2230/205* (2013.01); *A61M 2230/432* (2013.01); *A61M 2230/50* (2013.01); *A61M 2230/63* (2013.01); *A61M 2230/65* (2013.01)

(58) Field of Classification Search
  CPC .............. A61M 16/022; A61M 16/024; A61M 16/026; A61M 16/0666; A61M 16/0672; A61M 16/08; A61M 16/0816; A61M 16/0875; A61M 16/1005; A61M 16/14; A61M 16/147; A61M 16/16; A61M 2016/0018; A61M 2016/0021; A61M 2016/0024; A61M 2016/0027; A61M 2016/0036; A61M 11/00; A61M 11/005; A61M 11/02; A61M 2230/205
  See application file for complete search history.

(56) References Cited

U.S. PATENT DOCUMENTS

| | | | |
|---|---|---|---|
| 2005/0229926 A1 | 10/2005 | Fink et al. | |
| 2005/0284469 A1* | 12/2005 | Tobia | A61M 16/14 128/200.14 |
| 2007/0157931 A1* | 7/2007 | Parker | A61M 11/005 128/204.23 |
| 2007/0267010 A1* | 11/2007 | Fink | A61M 16/08 128/200.23 |
| 2008/0257337 A1* | 10/2008 | Denyer | A61M 16/14 600/533 |
| 2011/0180063 A1* | 7/2011 | Hunsicker | A61M 16/14 128/200.14 |
| 2015/0007817 A1 | 1/2015 | Longest et al. | |
| 2020/0139074 A1 | 5/2020 | Longest et al. | |

FOREIGN PATENT DOCUMENTS

| | | | |
|---|---|---|---|
| WO | 2011/077414 A2 | 6/2011 | |
| WO | 2011/077414 A3 | 6/2011 | |
| WO | 2011/077414 A9 | 6/2011 | |
| WO | 2013/163527 A1 | 10/2013 | |
| WO | WO-2015155342 A1 * | 10/2015 | ............ A61M 11/00 |
| WO | 2016/085354 A1 | 6/2016 | |

* cited by examiner

Tracheal dose v Aerosol duration interval

A line chart plots Tracheal dose (%) on the y-axis (0 to 30) versus aerosol duration intervals on the x-axis: Baseline 60LPM, Baseline 10LPM, 15 seconds, 10 seconds, 8 seconds, 7 seconds, 6 seconds, 5 seconds, 2 seconds.

Wet side (dotted): 2.15, 21.35, 24.31, 23.68, 21.52, 19.46, 16.32, 12.5, 15.29
Cannula (dashed): 1.58, 9.41, 20.29, 24.75, 21.96, 22.3, 23.87, 23.43, 14.9

Fig.7

Tracheal dose v Aerosol duration interval

A line chart plots Tracheal dose (%) on the y-axis (0 to 70) versus: Baseline at 60LPM, Baseline at 10LPM, 15 seconds, 10 seconds, 8 seconds, 6 seconds, 5 seconds.

No Phasic Delivery (dashed): 1.58, 9.41, 20.29, 23.68, 21.96, 23.87, 23.43
Phasic Delivery (solid): 53.04, 58.24, 61.67, 58.53, 50.59

Fig.8

GAS THERAPY SYSTEM FOR DELIVERY OF MEDICAMENT

CROSS-REFERENCE TO RELATED APPLICATIONS

This patent application is a continuation application under 37 CFR § 1.53(b) of and claims the benefit to U.S. application Ser. No. 16/621,560, filed Dec. 11, 2019, which is a national phase entry under 35 U.S.C. § 371 of International Application No. PCT/EP2018/067937, filed Jul. 3, 2018, which claims the benefit under 35 U.S.C. § 119 to European Application No. 17179658.4, filed on Jul. 4, 2017, the entireties of which are incorporated herein by reference.

INTRODUCTION

Field of the Invention

The invention relates to a gas therapy system for use where patients require respiratory support and/or supplemental oxygen. An example of such is a high flow nasal therapy (HFNT) system, in which the flow is directed through a nasal cannula.

Gas therapy such as high flow gas therapy is a growing therapy providing respiratory support to patients requiring breathing support and/or supplemental oxygen, in which delivered flow rates may be high, up to 60 L/min in many cases. The suggested mechanisms by which such systems provide respiratory support include:
  reduction of dead space, and
  positive airway pressure promoting more controlled breathing However the use of these relatively high flows does not facilitate optimal aerosol delivery and, low single figure deposition percentage efficiencies have been reported. In the past, the approach has often been complete removal of the patient from respiratory support in order to administer aerosol.

WO2015/155342 (Stamford Devices Ltd) describes a HFNT system in which there is increased aerosol delivery during patient inhalation, and reduction of gas flow during aerosol therapy.

The invention is directed towards achieving improved delivery of aerosol during high flow therapy.

SUMMARY OF THE INVENTION

We describe a gas therapy system comprising a flow line, a gas source or a link to a gas source, and a nebulizer or a link to a nebulizer for aerosol delivery, a patient interface or a coupler for connection to a patient interface, and a controller configured to modulate gas flow and aerosol delivery in real time.

The controller may be configured to change gas flow rate between at least one upper level and at least one lower level, and to dynamically stop or reduce aerosol delivery during gas flow at the upper level, and to dynamically activate or increase aerosol delivery during intervals of gas flow at the lower level.

Optionally, the controller is configured to switch between said levels in each of a succession of cycles, in which each cycle has specific upper and lower gas flow rate levels.

Optionally, said cycles have durations in the range of 1 second to 2 hours.

Preferably, the system is configured to provide aerosol delivery with switch-on and/or switch-off durations under 25 ms, preferably under 10 ms.

The system may be configured to provide a gas flow switching duration of under 100 ms, preferably under 50 ms.

Preferably, the system comprises a sensor to detect patient inhalation and/or exhalation, and the controller is configured to provide aerosol delivery primarily during inhalation. Optionally, said sensor is a pressure sensor. The sensor may be mounted adjacent to or in the patient interface or coupler. The sensor may include a temperature sensing device, preferably mounted in the patient interface or adjacent to the coupler.

Preferably, the sensor includes a humidity sensing device, preferably mounted in the patient interface or adjacent to the coupler. The sensor may include one or more selected from a movement detector, a diaphragm displacement sensor, an ultra-wideband sensor, an impedance plethysmography sensor, a respiratory inductance plethysmography sensor, and an elastomeric plethysmography sensor. Preferably, the sensor includes a gas or volatiles sensing device. The sensor may be adapted to detect carbon dioxide or a tracer gas or volatile delivered in the gas flow.

Optionally, the system is adapted to generate a bolus of aerosol within the flow line for optimal aerosol delivery during inhalation, preferably in advance of and including the start of peak inhalation.

The controller may be configured to determine an optimal duration for the interval by calculating a value for internal circuit volume between the aerosol generator and the end of the patient interface or coupler divided by the gas flow rate, to determine time required for aerosol generation through to delivery at the patient interface.

Preferably, the controller is configured to dynamically calculate optimal aerosol generation and/or gas flow parameters dependent on location in the flow line of the aerosol generator.

The controller may be configured to perform modulation of oxygen supplied during the intervals to maintain a desired patient blood oxygenation. The system may include a real time pulse oximeter and an oxygen regulator to perform said modulation.

Optionally, the system comprises a humidifier located adjacent to the aerosol generator. The aerosol generator may be placed adjacent to or in the patient interface or coupler. Preferably, the patient interface includes a nasal cannula for nasal delivery as a high flow nasal therapy system.

Optionally, the controller is configured to provide aerosol delivery during only a sub-set of inhalation periods, but for sufficient time to minimise risk of insufficient PEEP (positive end expiratory pressure) which may manifest as lung de-recruitment.

The upper flow rate may be in the range of 40 LPM and 80 LPM, preferably 50 LPM to 70 LPM, and the lower flow rate is in the range of 1 LPM and 20 LPM, preferably 5 LPM to 15 LPM.

Preferably, the duration of said intervals is in the range of 5 seconds to 20 seconds. Said duration may be 8 seconds to 15 seconds.

Optionally, the controller is configured to switch to the lower gas flow level in advance of commencement of inhalation, by a time $\Delta 1$. Preferably, $\Delta 1$ has a value in the range of 0.01 seconds to 3.0 seconds. Preferably, the controller is configured to activate aerosol generation during said interval a time duration $\Delta 2$ after switching to the lower gas flow level. Preferably, the time duration $\Delta 2$ has a value in the range of 0.01 seconds to 3.0 seconds. Optionally, the controller is configured to de-activate the aerosol generation a time duration Δ3 before end of inhalation. Preferably, Δ3 has a value in the range of 0.01 seconds to 3.0 seconds. Preferably, the controller is configured to raise the gas flow rate to the upper level a time duration Δ4 after end of inhalation.

Optionally, the system comprises a flow sensor in the flow line and the controller is configured to use output signals from the flow sensor to monitor gas flow from the gas source and to use said flow monitoring when controlling gas flow rate.

We also describe a method of operation of a controller of a gas therapy system comprising a flow line, a gas source or a link to a gas source, and a nebulizer or a link to a nebulizer for aerosol delivery, and a patient interface or a coupler for connection to a patient interface, the method comprising steps of the controller modulating gas flow and aerosol delivery in real time, in which the controller changes gas flow rate between at least one upper level and at least one lower level, and dynamically stops or reduces aerosol delivery during gas flow at the upper level, and dynamically activates or increases aerosol delivery during intervals of gas flow at the lower level.

Optionally, the controller switches between said levels in each of a succession of cycles, in which each cycle has specific upper and lower gas flow rate levels. Preferably, said cycles have a duration in the range of 1 second to 2 hours.

Optionally, the controller provides aerosol delivery with a switch-on or switch-off duration under 25 ms, preferably under 10 ms.

Preferably, the controller provides a gas flow switching duration of under 100 ms, preferably under 50 ms.

Additional Statements

According to the invention there is provided a gas therapy system comprising a flow line, a gas source or a link to a gas source, and a nebulizer or a link to a nebulizer for aerosol delivery, a patient interface or a coupler for connection to a patient interface, and a controller configured to modulate gas flow and aerosol delivery in real time. In the invention, the controller is configured to change gas flow rate between at least one upper level and at least one lower level, and to dynamically stop or reduce aerosol delivery during the upper gas flow rate durations, and to activate or increase aerosol delivery during the lower gas flow rate durations.

In one case the controller is configured to switch between said rates in each of a succession of cycles, in which each cycle has specific upper and lower gas flow rates.

Said cycles may have a duration in the range of 1 second to 2 hours.

In some cases the system is configured to provide aerosol delivery with a switch on or switch off duration under 25 ms, preferably under 10 ms.

In some embodiments the system is configured to provide a gas flow switching duration of under 100 ms, preferably under 50 ms.

In one case the system comprises a sensor to detect patient inhalation and/or exhalation, and the controller is configured to provide aerosol delivery primarily during inhalation.

Said sensor may be a pressure sensor.

In some cases the sensor is mounted in the patient interface such as a nasal interface.

In some cases the sensor includes a temperature sensing device, preferably mounted in the patient interface such as a nasal interface.

The sensor may include a humidity sensing device, preferably mounted in a patient interface such as a nasal interface.

In some cases the sensor includes a movement detector, a diaphragm displacement sensor, an ultra-wideband sensor, impedance plethysmography, respiratory inductance plethysmography or elastomeric plethysmography sensors.

In one case the sensor includes a gas or volatiles sensing device. The sensor may be adapted to detect carbon dioxide or a tracer gas or volatile delivered in tandem with the gas flow.

In some cases the controller is configured to control gas flow in a square, a ramp, a saw-tooth, a triangle or a constant profile for optimal aerosol delivery.

The system may be adapted to generate a bolus of aerosol within the flow line for optimal aerosol delivery during inhalation, preferably in advance of and including the start of peak inhalation.

The controller may be configured to determine an optimal duration of aerosol generation and the associated lower gas flow rate by calculating a value for internal circuit volume between an aerosol generator and the end of the patient interface such as a nasal interface divided by the gas flow rate, to determine time required for aerosol generation through to delivery at the patient interface such as a nasal interface.

In some cases the controller is configured to perform modulation of oxygen supplied during the lower gas flow rates to increase oxygen levels delivered during lower gas flow rate periods to maintain the consistency of blood oxygenation.

The system optionally includes a real time pulse oximeter and oxygen regulator to perform said modulation.

The controller may be configured to provide aerosol delivery during only a sub-set of inhalation periods but for sufficient time to minimise risk of insufficient PEEP (positive end expiratory pressure) which may manifest as lung de-recruitment.

In some cases the controller is configured to provide aerosol delivery chosen for a specific portion of inhalation periods, or at certain time intervals irrespective of number of inhalations during said intervals.

The system may comprise a heated humidifier/humidifier and the aerosol generator placed at or adjacent to same.

In some cases the system comprises a nasal cannula and the aerosol generator is placed at the nasal cannula.

The controller may be configured to dynamically calculate optimal aerosol generation and/or gas flow parameters dependent on location in the flow line of aerosol generation, for example fluidic volume of the flow line between the location of aerosol generation and exit geometry to patient divided by the gas flow rate being applied.

In some embodiments the system includes a nasal cannula for nasal delivery as a high flow nasal therapy system.

In some cases the upper flow rate is in the range of 40 LPM and 80 LPM, preferably 50 LPM to 70 LPM, and the lower flow rate is in the range of 1 LPM and 20 LPM, preferably 5 LPM to 15 LPM.

DETAILED DESCRIPTION OF THE INVENTION

Brief Description of the Drawings

The invention will be more clearly understood from the following description of some embodiments thereof, given by way of example only with reference to the accompanying drawings in which:—

FIG. 7 is a plot of tracheal dose vs aerosol interval duration for systems where the nebulizer is next to the humidifier and next to the cannula as shown in FIG. 1(b); and FIG. 8 is a pair of plots illustrating tracheal dose vs. aerosol interval duration with and without phasic delivery according to patient breath monitoring.

DESCRIPTION OF THE EMBODIMENTS

The invention is described below for a high flow nasal therapy ("HFNT") system, but it applies equally to other gas therapy systems especially including high flow systems such as CPAP, BiPAP, and resuscitation. The system performs integrated cycling in which a nebulizer and a gas flow are cycled in an inverse manner. For example, at higher flows of over 20 LPM (litres per minute) no aerosol will be generated, however, when the nebulizer is in operation the system will switch to a low flow of for example 10 LPM to facilitate greater aerosol deposition, while the nebulizer will be operating at maximum output. The gas flow will preferably not decrease to zero so as to reduce but not eliminate the respiratory support.

Figure 1A:
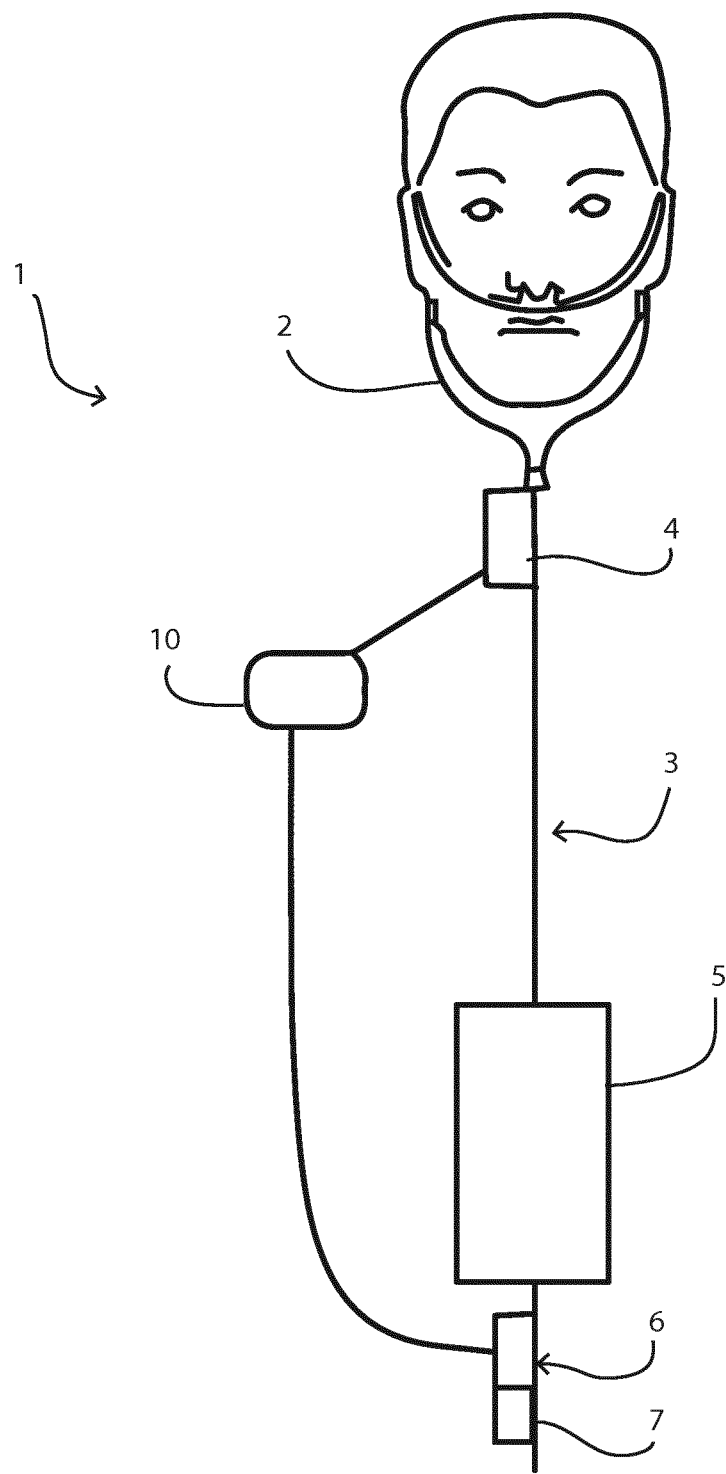
FIG. 1(a) is a diagram showing a HFNT system of the invention connected to a patient.
Figure 1B:
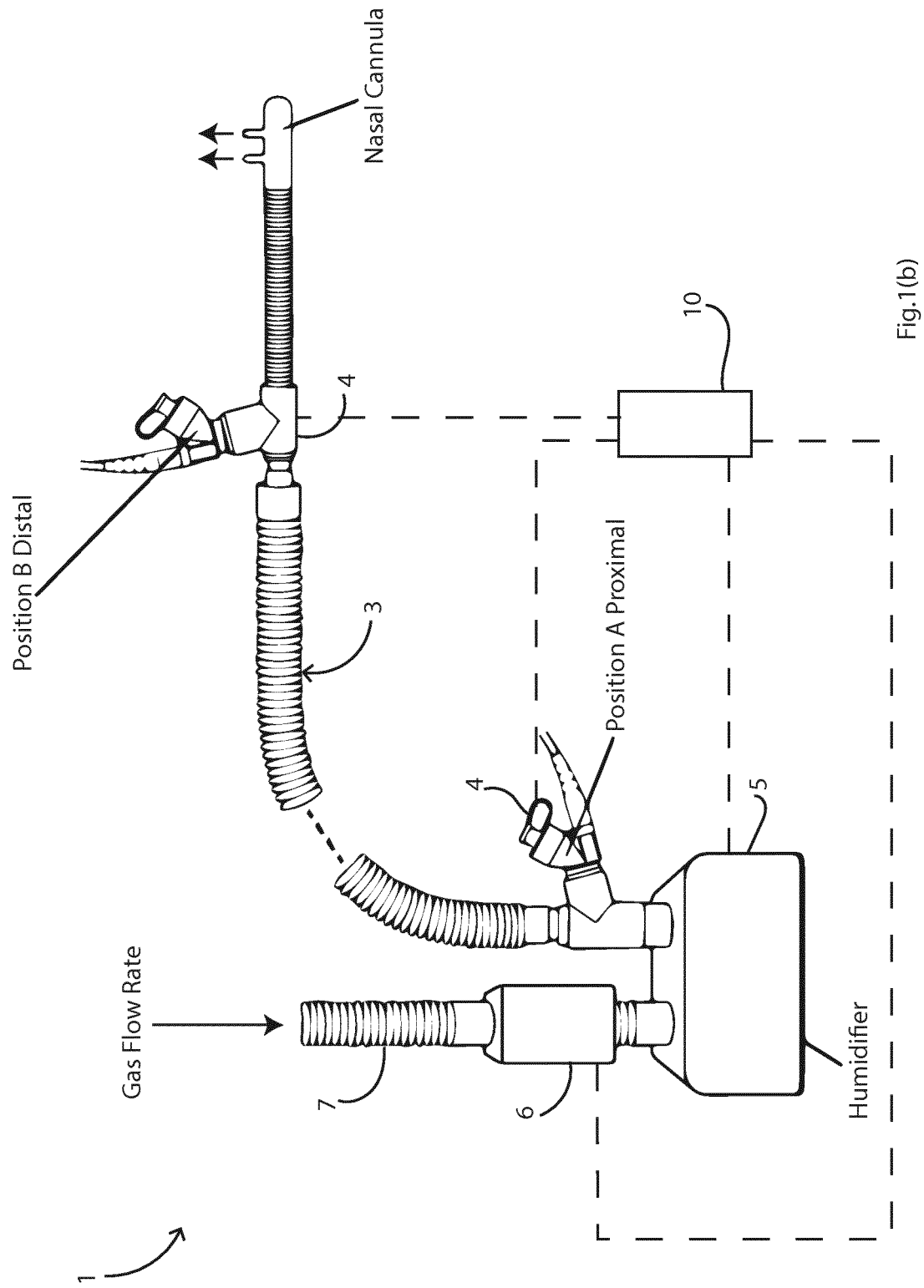
FIG. 1(b) is a view showing the physical arrangement and an alternative arrangement.

Referring to FIGS. 1(a) and 1(b) a HFNT system 1 comprises a nasal cannula 2 supplied by a flow line 3 including a nebulizer 4 and a heated humidifier 5. The line 3 has an air inlet 7 alongside which there is a flow meter/regulator 6. The gas source could be supplied from a gas blender, directly connected to medical gas supply or from a flow blower or turbine. FIG. 1(a) shows in diagrammatic terms the arrangement where the nebulizer is near a cannula. FIG. 1(b) shows the physical arrangement and also shows an alternative use in which the nebulizer 4 is close to the humidifier 5 (Position A, Proximal). This shows versatility of the system in use, and the description below describes the aspects which arise from these different nebulizer positions.

A programmed controller 10 is linked with the nebulizer 4, the air inlet 7, and the flow meter/regulator 6 to perform dynamic real time control, as described below. A user interface may be incorporated as part of the controller 10, or be linked by cable or wireless such as Bluetooth. Unidirectional flow is from the air inlet 7 towards the nasal interface 2 via a single main limb 3 that may split into two sides at the nasal interface 2.

The system control unit 10 houses a digital processor programmed to control a flow blower or turbine linked with the inlet 7, to, control the gas flow from the gas inlet 7 and into the humidifier. Hence, the controller 10 can control the rate of gas flow, and this is achieved with short ramp times to reach the target rates, typically in the range of 50 ms to 100 ms. The majority of treatment time is with gas flow at the higher rate (e.g. 60 LPM), and this flow is interrupted at intervals with lower flow rates (e.g. 10 LPM, 30 LPM). Where patients are too ill to be able to cope with a reduction to the order of 10 LPM, the lower level may for example be higher such as a value in the range of 20 LPM to 40 LPM.

There is aerosol delivery during these intervals. The intervals are preferably triggered at target times according to the extent of required aerosol therapy. Preferably, the intervals are automatically chosen to coincide with patient inhalation.

It is envisaged that in some cases the cycle will be 60 seconds, with one interval in each such cycle for a minority of the 60 seconds.

Flow control may alternatively be achieved by restriction of a flow orifice by electronic control such as a solenoid valve. Such electronic control is also capable of response times in the region of 50 ms to 100 ms.

The system may include a flow sensor linked with the controller and being at any location between the gas source and the cannula, for detection of the gas flow from the gas source. This may be used by the controller in its operations to automatically trigger aerosol delivery in addition to or instead of using the valve control signals.

The controller 10 is also connected to the aerosol generator 4 for on/off actuation.

The aerosol delivery is controlled to turn on or turn off in a duration under 25 ms, preferably under 10 ms. The gas flow is controlled with a ramp up or a ramp down duration of under 100 ms, preferably under 50 ms.

During high flow therapy at higher gas flow rates (range 10 to 60 LPM for example), the aerosol generator 4 operation is controlled to stop or reduce rate of aerosol generation.

During high flow therapy at lower gas flow rates (range 1 to 10 LPM for example), the aerosol generator operation is controlled to maximise aerosol output.

If the user selects a suboptimal gas flow rate (with regards to aerosol delivery) during periods in which the aerosol generator 4 is in operation, the controller 10 acts to control the gas flow rate.

The system maintains respiratory support with the prescribed upper gas flow rate for the majority of time, but with intermittent short periods of respiratory support with lower gas flow rates. It is during these intermittent, lower gas flow rate intervals only that aerosol is generated.

In the past, the approach has often been complete removal of the patient from high flow respiratory support to administer aerosol using a handheld, or other aerosol delivery system. The invention is therefore very advantageous by allowing for the maintenance of respiratory support during aerosol delivery and mitigating the risk of potential de-recruitment of the lung during periods of low or no gas flow during aerosol therapy.

In other embodiments the system also includes sensors such as sensors to detect patient breathing cycles, as described in more detail below. There may be sensors to detect patient physiological parameters which indicate extent of real time need for gas therapy and/or aerosol therapy. Delivery of aerosol on a breath-activated basis is referred to as "phasic delivery". The vast majority of aerosol being delivery during inhalation, for optimum tracheal dose efficiency.

In overview, the controller switches between upper and lower levels of gas flow rates, and activates aerosol delivery during some or all of the time that the gas flow is at the lower rate. This is in some embodiments based on time cycles, such as a cycle of 45 seconds, 30 seconds being upper rate and 15 seconds being lower rate. There may be dynamic changes to this depending on user inputs at the UI and/or sensed conditions such as a pressure or humidity sensor detecting patient inhalation and/or sensors to detect a patient condition indicating when gas flow needs to switch to the upper rate. The controller may apply a completely manual over-ride in certain situations.

TABLE 1

Control algorithm calculations.

| Example | Fluidic volume (mL) | | | | Gas Flow Rate (LPM) | Time for aerosol to travel from aerosol generator to patient (secs) |
|---|---|---|---|---|---|---|
| Location of aerosol generator | Humi- difier | Tubing | Patient interface | Total Volume (Liters) | | |
| Dry side of humidifier | 150 | 250 | 5 | 0.405 | 60 | 0.41 |
| | 150 | 250 | 5 | 0.405 | 10 | 2.43 |
| At patient interface | n/a | n/a | 5 | 0.005 | 60 | 0.01 |
| | n/a | n/a | 5 | 0.005 | 10 | 0.03 |

Examples of calculations used in the control of the gas flow and aerosol generation are presented in Table 1. These worked examples illustrate the differences in transit time through the system relative to the position of the aerosol generator 4 and gas flow rate.

The intervals for aerosol delivery (with lower gas flow) may be as short as only 2 minutes per hour or less, depending on the clinical situation. The nebuliser duty cycle may be for example 5%, 10%, or 20%, and in general it is preferred if it is in the range of about 2% to 50% for optimum dose efficiency.

Further, the aerosol generator shall not affect the flows or pressures being applied to the patient. For example, preferred aerosol generators include, but do are not limited to, static or actively vibrating mesh nebulisers, surface acoustic wave aerosol generators, Fourier horn-type aerosol generators. An example of a non-preferred aerosol generator is the jet-type nebulisers that require a driving gas for operation.

The following describes the invention in more detail.

Figure 2:
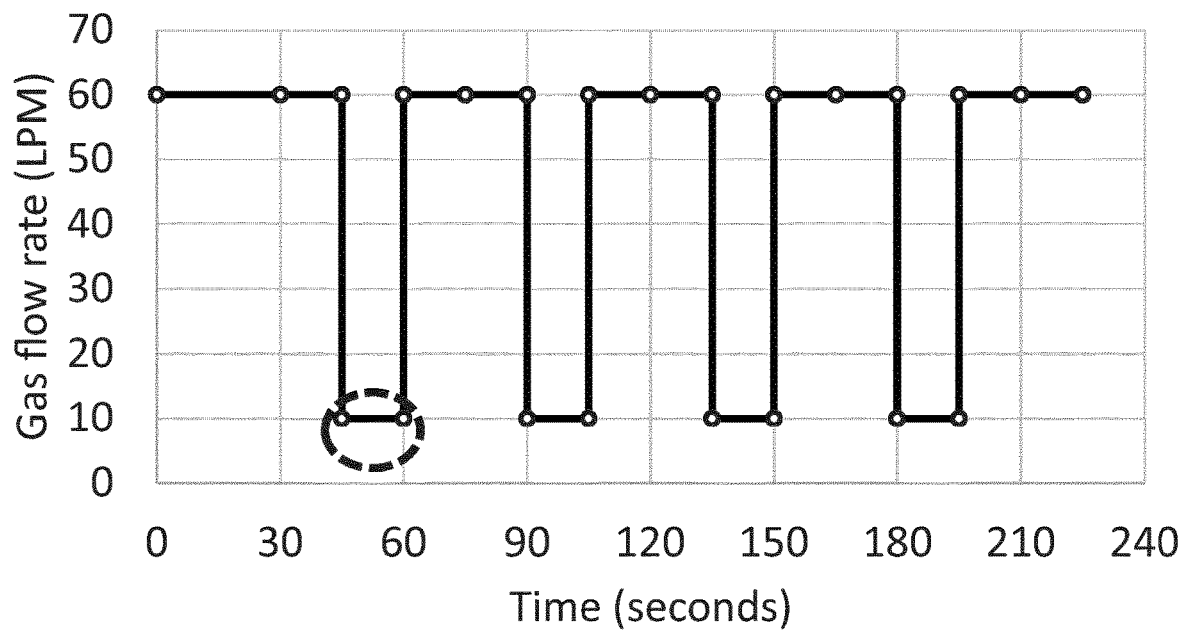
FIGS. 2 to 4 are plots showing gas flow rate versus time for examples of use of the system.
Figure 3:
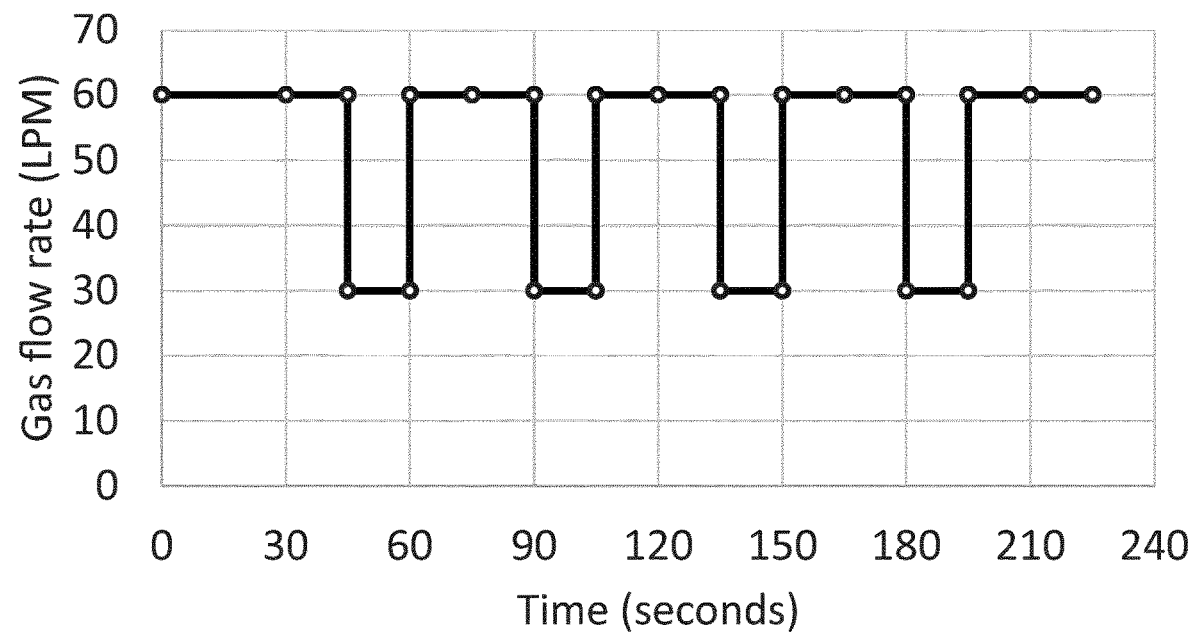
Figure 4:
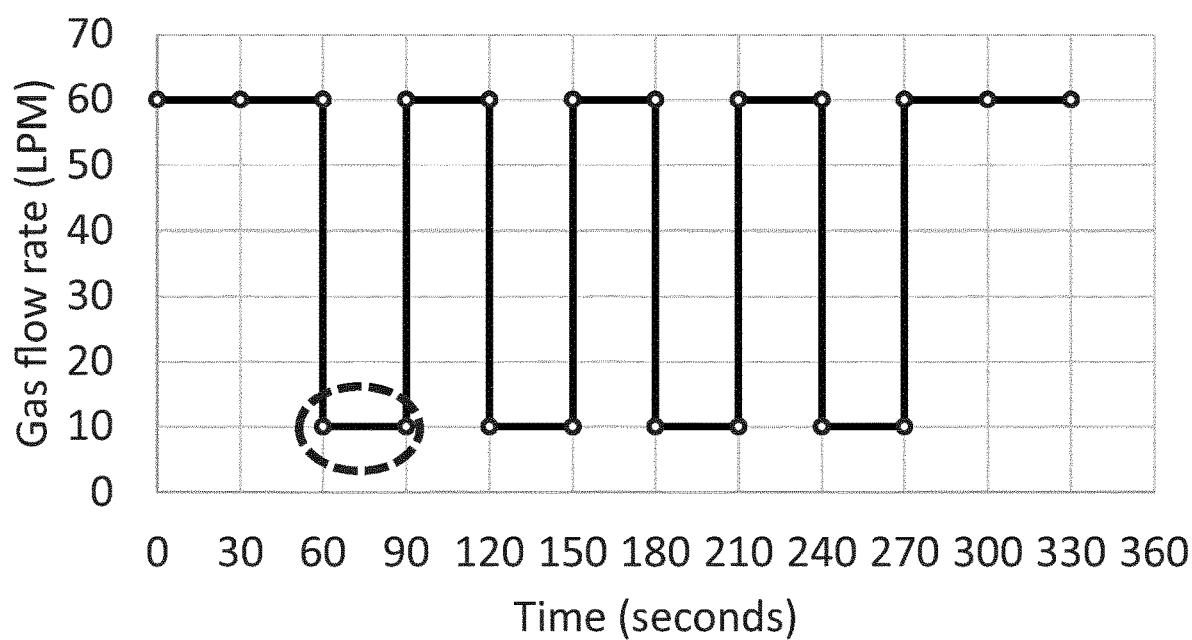

FIG. 2 is an illustration of gas flow rate delivered to the patient at 60 LPM and 10 LPM, with a 60 LPM period of 30 s (seconds) and a 10 LPM interval of 15 s making up each cycle. FIG. 3 shows a control scheme in which the switching is for the same time periods, but the lower rate is 30 LPM. FIG. 4 shows a scheme in which the periods are equal, 30 s, and the rates are 60 LPM and 10 LPM.

The optimal duration of aerosol generation and the associated lower gas flow rate (in minutes or seconds), is in one example depending on, among other parameters, output of a calculation of internal circuit volume between the nebuliser 4 and the end of the nasal interface 2 divided by the gas flow rate. Sufficient time is required for aerosol generation, transit through the internal tubes and delivery beyond the nasal interface. The relative periods of optimal and suboptimal gas flow rates may change, and the examples provided herein are for illustration purposes only.

As shown in FIG. 1(b) the aerosol generator may be placed: (a) at the nasal interface, (b) between the nasal interface and the circuit tubing, or (c) attached to the humidifier (which may or may not be heated) and/or the gas flow generator/source.

The tracheal dose, i.e. amount of aerosol inhaled by a simulated patient and captured at the level of the trachea, characterised across low and high gas flow rate settings commonly used in Adults, and the improved method are presented in Table 2 below.

Tracheal Dose

TABLE 2

Tracheal dose.

| | | Tracheal Dose (%) | |
|---|---|---|---|
| | Gas Flow (LPM) | 3.3 µm Droplet Size | 4.5 µm Droplet Size |
| Dosing examples | 60 | 3.45 ± 0.47 | 2.15 ± 0.13 |
| | 30 seconds of 60 LPM + 15 seconds of 30 LPM | 10.43 ± 0.88 | 7.98 ± 0.69 |
| | 30 seconds of 60 LPM + 15 seconds of 10 LPM | 31.74 ± 1.15 | 25.15 ± 0.52 |
| | 30 seconds of 30 LPM + 15 seconds of 10 LPM | 25.86 ± 2.05 | 19.44 ± 0.93 |

The tracheal dose is the drug mass delivered to the level of the trachea in a bench model of a breathing adult patient (15 BPM (breaths per minute), Inspiratory:Expiratory (I:E) ratio of 1:1, and a tidal volume (Vt) of 500 mL), expressed as a percentage of the nominal dose placed in the aerosol generator medication cup.

In the examples above, the higher gas flow was run for 30 seconds and the lower gas flow was run for 15 seconds. These durations are to be considered an example of the available options. As described in more detail below, the control scheme may be based on different time periods or may be based on active sensing of a patient, such as according to breaths.

In Table 2 it is noted that decreasing gas flow rate facilitates an increase in tracheal dose. This is however at the considerable expense of much reduced gas flow therapy, which in many clinical situations is not possible without risk to the patient. It is also noted that a 3.3 µm (Dv50) droplet size (emitted from the aerosol generator) facilitates an increase in tracheal dose over a 4.5 µm (Dv50) droplet size.

Switching of gas flow between upper and lower rate levels and generation of aerosol only during those lower gas flows, facilitates a higher tracheal dose than that recorded for the high gas flow rate. Moreover it also, surprisingly, achieves a higher tracheal dose than would be the case for a continuous lower gas flow rate level. The dose proportion delivered is about 26% when the gas flow rate is continuously 10 LPM, whereas when it is switched between 60 LPM and 10 LPM in cycles with periods of 30 s and 15 s respectively the proportion of dose delivered is about 32%. Again, lower droplet size facilitates a greater tracheal dose.

Whilst the differential between reducing the flow from 60 to 30 LPM is not as great as reducing flow from 60 LPM to 10 LPM, this still demonstrates that there are benefits even while reducing the flow from the high value of 60 LPM to a lower flow.

Also, it is envisaged that with lower sized droplets, e.g. in the range of 0.5 µm to 4.0 µm (e.g. 3.3 µm) as compared to about 4.5 µm there may be significant benefits with respect to delivered dose.

In another embodiment, the system performs breath control of aerosol delivery, in which the aerosol generator is only active in periods of inhalation during which concurrent reduction in gas flow is imposed. Therefore, aerosolising during the exhalation phase is avoided, reducing possible drug wastage. Another aspect is that higher gas flow rates tend to reduce the number of breaths per minute and so this may be a significant source of delivery variation addressed with breath control. In one example control scheme, the controller activates the nebulizer only when both the assigned time period (such as 15 s in a 45 s cycle) is reached and there is inhalation. In another example, the controller activates the nebulizer and reduces gas flow only during inhalation in a sub-set of the total inhalations, such as every second inhalation or every third inhalation. Inhalation is preferably sensed in real time by pressure sensors in the cannula or the limb leading to the cannula. The sensor may detect thoracic or abdominal movement resultant from respiratory movements, such sensors include but are not limited to: Graseby respiration sensor, ultra-wideband, impedance plethysmography, respiratory inductance plethysmography or elastomeric plethysmography device.

Figure 5:
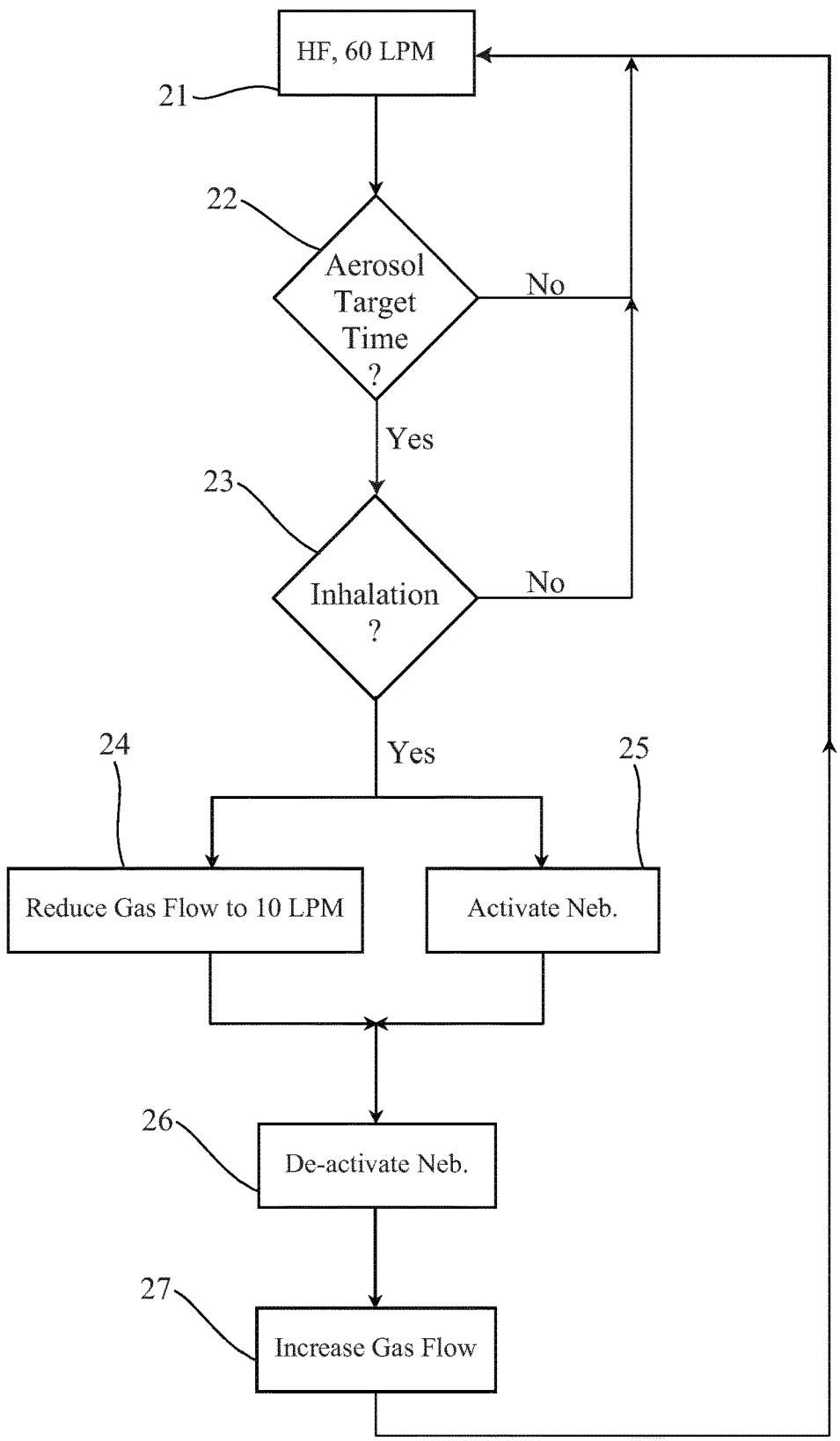
FIG. 5 is a flow diagram for operation of the system in one example.
Figure 6:
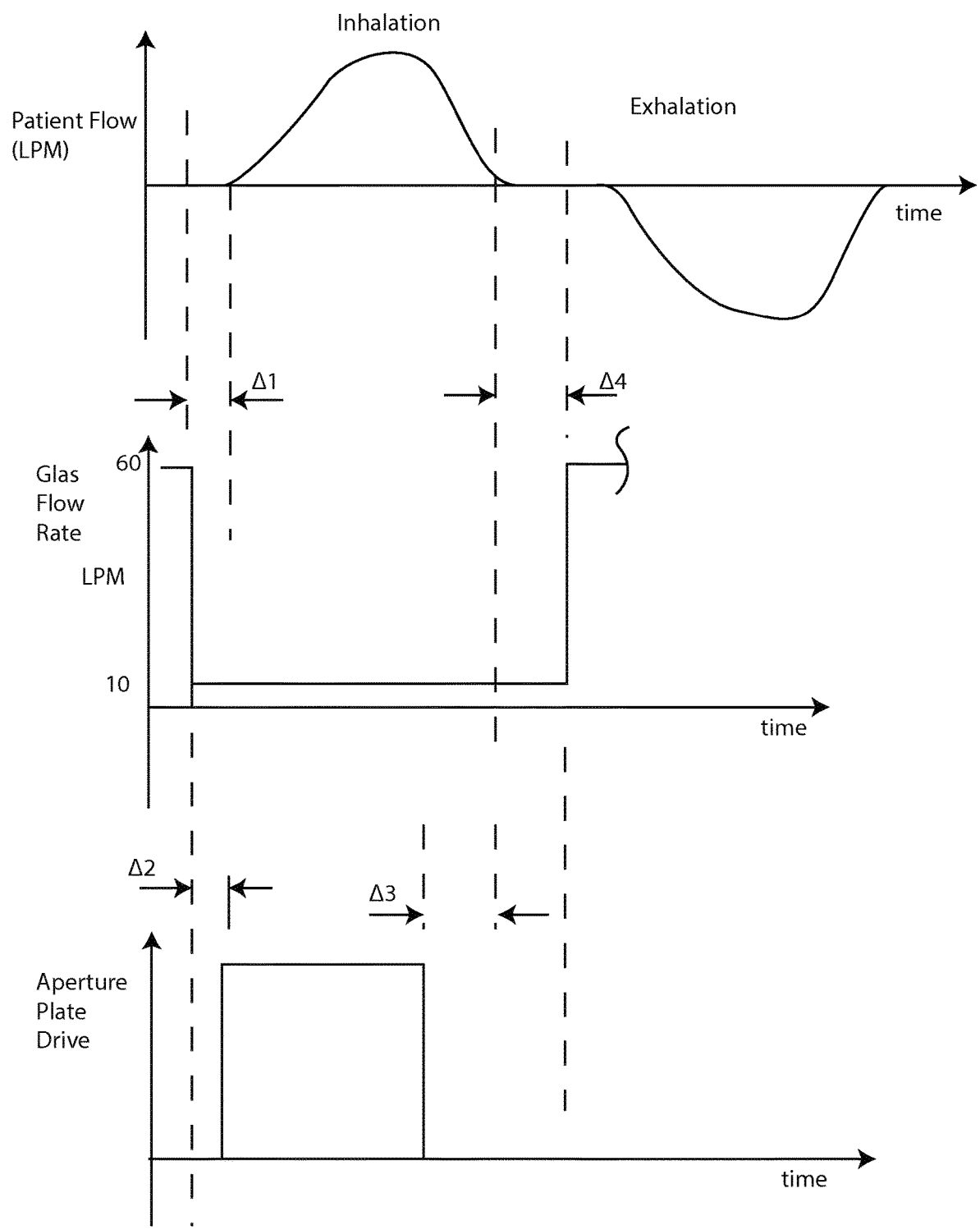
FIG. 6 is a series of plots illustrating relationships between patient breathing, gas flow, and aerosolization.

Referring to FIGS. 5 and 6 in a method 20 performed by the digital processor of the controller 10 there is aerosol generation only when a target aerosolization time has arrived and there is patient inhalation. Step 21 represents the normal high gas flow rate level of 60 LPM for patient treatment to ensure that there is sufficient delivery of oxygen to the lungs, clearance of the 4 dead space of CO2 and maintenance of airway pressure. Step 22 indicates the monitoring of time since start of treatment when it is preferred that aerosol be delivered, according to clinical requirements. If so, then the controller determines in step 23 according to the breathing sensors if there is inhalation. If so, the controller both reduces gas flows to only 10 LPM in step 24 and activates the nebulizer in step 25. In this example there is phasic delivery with aerosolization only when there is patient inhalation. However, in other examples this is not essential.

These aspects are illustrated in FIG. 6. The top plot shows detected inhalation, represented as positive flow and exhalation as negative flow (could be opposite). Below that, the plot illustrates gas flow dropping from 60 LPM to 10 LPM as inhalation begins.

There is a small extent of advance dropping of the gas flow (Δ1) due to inhalation being predicted. The prediction may be based on the detected breathing pattern, with a predicted "breaths per minute" (BPM) rate. For example, if there are 10 breaths per minute the cycle time is 6 seconds, indicating an inspiration time of 3 seconds and a dwell time before exhalation.

Then, as shown in the bottom plot aerosol delivery is activated after a short delay of Δ2 from gas flow reduction. Aerosol delivery remains for a time direction well within the inhalation duration, ending Δ3 before end of inhalation. Then, after a delay of Δ4 from end of inhalation the gas flow returns to 60 LPM, thus ending the interval.

Δ1 is not essential, but is preferred in order to ensure that the conditions are correct for time duration of 0.01 s to 3.0 s for aerosolization.

Also, Δ2 is not essential, but is preferred to ensure that optimum conditions exist for aerosolization. It is preferably short, in a range of about 0.01 s to 3.0 s. The value of Δ2 can be set according to desired penetration of the medicament. For example it can be very short or non-existent for particular targeting of the peripheral airways. It can be longer where the target is the conducting airway region, and it can be long if the target is the upper airway region.

Δ3 is a delay between end of aerosolization and end of inhalation. It may have a value in the range of 0.01 s to 3.0 s for the reasons given above for Δ2.

Δ4 depends on the length of dwell between inhalation and exhalation. It is preferred to have this delay short enough in order to avoid low flow during exhalation.

In other embodiments, the sensor includes a gas or volatile sensing device. Gases being detected may include, but are not limited to; carbon dioxide, a tracer gas/volatile delivered in tandem with the high flow, and nitric oxide.

The upper level gas flow duration may be from about 70% to about 99% of each cycle. For example, for a 5 sec cycle at 80% this equates to 4 sec period with upper level gas flow and no aerosol, and 1 second with lower gas flow rate and with aerosol delivery. It is preferred that the duty cycle for upper rate flow to lower level flow is 65% to 35%.

In a further case the system performs modulation of oxygen supplied during the lower gas flow rates, i.e. if the patient requires X % oxygen and that is delivered at 60 LPM, then 10 LPM gas flow will deliver less oxygen. Therefore increasing oxygen concentration in the gas flow during the lower gas flow rate interval may act to maintain the consistency of blood oxygenation. To achieve this, the system may include a real time pulse oximeter, an oxygen regulator, and/or a blender. In many cases the oxygen concentration is as high as 95%, and so there is little scope to increase it in the intervals. However, the benefit of increasing the oxygen concentration of the gas mix supplied during the intervals (air and oxygen, or Helium and oxygen) is more pronounced where the concentration at the higher flow rate level is less, say in the range of 50% to 80%. In this aspect the oxygen concentration control may be at least partly in response to detected $SpO_2$ levels.

Preferably, the controller executes an algorithm to calculate a value for time aerosol takes to move from the aerosol generator to the end of cannula, and to add sufficient time for a breath. This will help determine the length of time for each period of the lower gas flow rate. Table 1 above gives exemplary data on which this can be based.

In many cases the intervals of aerosol delivery are not every breath. For example, the system may be set to deliver aerosol once every X number of minutes. X is preferably determined according to the risk of lung de-recruitment. Preferably, the controller includes stored patient-specific settings which it uses to automatically determine frequency of aerosol delivery.

The system may in some examples generate a bolus of aerosol within the flow line for optimal aerosol delivery during the lower gas flow rates. This may be achieved by the gas flow line being divided into two limbs, one for aerosol delivery and the other for only gas flow. The bolus of aerosol is built up by operation of the nebulizer while the aerosol limb is closed, and this limb is opened during lower level gas flow.

In other examples, the controller is configured to manage flows according to inertial potential of the aerosol.

The volume of aerosol losses within the circuit and the consequent emitted dose, available for inhalation by the patient, is controlled by the aerosol droplet or particle size produced by the aerosol generator and the relative density of aerosol droplets or particles in the gas flow. Specifically, droplets or particles are smaller than the cut-off size imposed by the patient interface, e.g. nasal cannula size combined with the chosen gas flow or range of gas flow rates and the output from the aerosol generator is controlled such that the risk of inertial impaction within the circuit tubing is reduced.

The advantage of both droplet size and nebulizer duty cycle is reduced at higher gas flow rates. Therefore the combination of lower gas flow rate with lower droplet or particle size and lower nebulizer duty cycle provides major benefits. For example, it is preferred that the droplet size be in the range of 1.0 μm to 4.0 μm and that the nebulizer duty cycle be in the range of 2% to 20%. For example 5% duty cycle may be 5 microseconds ON, 95 microseconds OFF;

10% duty cycle may be 10 microseconds ON, 90 microseconds OFF; and 20% duty cycle may be 20 microseconds ON, 80 microseconds OFF).

In other examples, assuming a range of 5 to 50 breaths per minute, this means that at 5 BPM, each breath cycle will be 12 seconds in duration. ~50 BPM, each breath will be 1.2 seconds long. If the system does not utilise breath controlled aerosol delivery, aerosol ON for 15 seconds will align with approximately 1.25 breaths for 5 BPM and 12.5 breaths for 50 BPM. If the system does utilise breath controlled aerosol delivery the I:E ratio may be as much as 1:5:

@5 BPM=12 seconds⇒2 seconds inhale
@50 BPM=1.2 seconds⇒0.20 seconds inhale

With phasic (breath-actuated) delivery the duty cycle is variable, being responsive to current patient breathing pattern.

FIG. 7 shows test results for tracheal dose for the two possible set-ups shown in FIG. 1(b)—"Wet-side" just downstream and next to the humidifier, (Position A, Proximal), and "Cannula" (Position B, Distal). There is no breath detection control in these tests.

Wet Side

The "baseline" tracheal dose (when the gas flow and aerosol generation remains constant) is 21% for 10 LPM and 2% for 60 LPM. Unsurprisingly the efficiency is very low for continuous 60 LMM gas flow, which is part of the problem addressed by the invention. The tracheal dose improves considerably when the flow rate is down to 10 LPM, however this is not always practical because the higher rates are needed for patent respiratory support.

With intervals as described for operation of the controller the dosage results remain good and indeed improve for intervals of between 15 secs and about 7 secs. However, for shorter intervals the dosage results fall off.

Cannula Side

Again, dosage is very poor for the baselines, in fact worse here for the 10 LPM continuous delivery. An important aspect is that the delivered dose does not drop off as the intervals decrease—still about 23% for intervals of 5 secs. It only drops significantly towards shorter intervals of about 2 seconds.

The data plotted in FIG. 7 is given below in Tables 3 and 4, in which "P-Value" is a unit-less representation of statistical significance of the difference between the columns, in which the lower the P-value the more significant it is, and a value of less than 0.5 is considered significant.

TABLE 3

|  | Tracheal dose (%) nebuliser at wet side | Tracheal dose (%) nebuliser at nasal cannula |
|---|---|---|
| Baseline at 10 LPM | 21.35 ± 0.23 | 9.41 ± 0.49 |
| Baseline at 60 LPM | 2.15 ± 0.13 | 1.58 ± 0.12 |

TABLE 4

| Aerosol duration at 10 LPM | Tracheal dose (%) nebuliser at wet side | Tracheal dose (%) nebuliser at nasal cannula | P-value |
|---|---|---|---|
| 15 seconds | 24.31 ± 0.69 | 20.29 ± 0.70 | 0.01 |
| 10 seconds | 24.76 ± 2.52 | 23.68 ± 1.27 | 0.72 |
| 8 seconds | 21.52 ± 0.42 | 21.96 ± 1.06 | 0.71 |
| 7 seconds | 19.46 ± 0.66 | 22.30 ± 2.16 | 0.26 |
| 6 seconds | 16.32 ± 0.78 | 23.87 ± 2.14 | 0.03 |

TABLE 4-continued

| Aerosol duration at 10 LPM | Tracheal dose (%) nebuliser at wet side | Tracheal dose (%) nebuliser at nasal cannula | P-value |
|---|---|---|---|
| 5 seconds | 12.50 ± 1.17 | 23.43 ± 0.47 | 0.00 |
| 2 seconds | 15.30 ± 0.92 | 14.90 ± 0.93 | 0.78 |

If the controller processor is programmed as shown in FIG. 5 to provide phasic delivery (upon detected inhalation) the tracheal dose results improve significantly, as shown in FIG. 8 and in Table 5 below. For all measurements the nebulizer was at the cannula (Position B, Distal in FIG. 1(b)).

TABLE 5

| Aerosol duration interval at 10 LPM | No Phasic Delivery | Phasic Delivery | P-value |
|---|---|---|---|
| 15 seconds | 20.29 ± 0.70 | 53.04 ± 11.38 | 0.01 |
| 10 seconds | 23.68 ± 1.27 | 58.24 ± 6.78 | 0.00 |
| 8 seconds | 21.96 ± 1.06 | 61.67 ± 5.15 | 0.00 |
| 6 seconds | 23.87 ± 2.14 | 48.82 ± 8.51 | 0.01 |
| 5 seconds | 23.43 ± 0.47 | 50.59 ± 6.73 | 0.00 |

In this case the dosage is in the range of about 50% to 60% for intervals of 15 s to 5 s, with high flow at 60 LPM for 30 s between each dosage interval.

Effect of Nebuliser Position on Aerosol Efficiency During Phasic Delivery

Efficient and less efficient aerosol durations were selected; 8 seconds and 5 seconds respectively. In order to compare the effect of nebuliser position during phasic delivery, the nebuliser was positioned at the wet side of the humidifier for 8 second and 5 second aerosol durations. Results are outlined in Table 6.

TABLE 6

| Aerosol duration at 10 LPM | Nebuliser at cannula | Nebuliser at wet side | P-value |
|---|---|---|---|
| 8 seconds | 61.67 ± 5.15 | 8.33 ± 2.00 | 0.003 |
| 5 seconds | 50.59 ± 6.73 | 6.96 ± 2.00 | 0.004 |

Table 6 shows tracheal dose (%) at the 8-second and 5-second aerosol duration settings when the nebuliser was placed at the wet side of the humidifier and at the nasal cannula. P-values are included to indicate significance. P-values of <0.05 are considered statistically significant.

Effect of Droplet Size on Aerosol Efficiency During Phasic Delivery

The preferred range for droplet size is approximately 1 μm to 10 μm.

Efficient and less efficient aerosol durations were selected; 8 seconds and 5 seconds respectively. In order to compare the effect of droplet size during phasic delivery, a nebuliser of low VMD was tested for the 8 second and 5 second aerosol durations. Results are outlined in Table 7 below.

TABLE 7

| Aerosol duration at 10 LPM | Standard VMD | Low VMD | P-value |
|---|---|---|---|
| 8 seconds | 61.67 ± 5.15 | 61.96 ± 4.20 | 0.94 |
| 5 seconds | 50.59 ± 6.73 | 54.90 ± 9.56 | 0.56 |

Table 7 shows tracheal dose (%) at the 8 second and 5 second aerosol duration settings. P-values are included to indicate significance. P-values of <0.05 are considered statistically significant.

In summary, tracheal dose was assessed during HFNT at the following gas flow rates: 60 LPM for 30 seconds with intervals of aerosol delivery at 10 LPM for several durations. Aerosol delivery was more efficient when the nebuliser was placed at the nasal cannula (~23%), compared to when placed at the wet side of the humidifier (~19%).

Phasic aerosol delivery was tested using the same gas flow controller set-up. The nebuliser was placed at the nasal cannula. A significantly greater tracheal dose was observed with phasic delivery (~58%), compared to without phasic delivery (~23%). Statistically significant differences were observed across all aerosol durations.

Optimal aerosol delivery was achieved when the nebuliser was placed at the nasal cannula, and when aerosol was delivered in a phasic manner. A nebuliser of low droplet size was associated with a marginal increase in tracheal dose. Phasic delivery method yielded high aerosol efficiency.

The system as described may be a discrete standalone assembly, interposed between a remote gas supply, e.g. wall gas or turbine, and the humidifier and patient circuit. Alternatively, it may be integrated in a ventilator system wherein aerosol generator operation and cycle time can be adjusted independently or by a pre-determined algorithm. Such a system provides ease of use benefits to the user.

It will be appreciated that the invention provides for very effective delivery of aerosol for treatment of a patient who is undergoing high flow gas treatment, despite the challenges that such gas flow presents. It achieves the aerosol treatment with only minimal effect on the gas flow for provision of oxygen and elimination of CO2 dead spaces.

The invention is not limited to the embodiments described but may be varied in construction and detail. For example, the flow line may comprise two or more branches, preferably unidirectional towards the nasal cannula. Components described for some embodiments may be used in other embodiments as will be apparent to those skilled in the art.

The invention claimed is:

1. A gas therapy system comprising a flow line, a gas source or a link to a gas source, and a nebulizer or a link to a nebulizer for aerosol delivery, a patient interface or a coupler for connection to a patient interface, and a controller configured to modulate gas flow and aerosol delivery in real time,
wherein the controller is configured to change gas flow rate from the gas source and perform modulation of (1) aerosol delivery from the nebulizer, and (2) a concentration of oxygen supplied from the gas source, based on the change in gas flow rate.

2. The gas therapy system as claimed in claim 1, wherein the controller is configured to switch between levels of gas flow rate in at least one cycle, the at least one cycle having a specific upper gas flow rate level and a specific lower gas flow rate level.

3. The gas therapy system as claimed in claim 2, wherein the upper gas flow rate level is in a range of 40 LPM and 80 LPM.

4. The gas therapy system as claimed in claim 2, wherein the at least one cycle has a duration in a range of 1 second to 2 hours.

5. The gas therapy system as claimed in claim 1, wherein the system is configured to provide aerosol delivery with a switch-on or switch-off duration under 25 ms, and to provide a gas flow switching duration of under 100 ms.

6. The gas therapy system as claimed in claim 1, further comprising one or more sensors configured to detect patient inhalation and/or exhalation, and wherein the controller is configured to provide aerosol delivery primarily during inhalation.

7. The gas therapy system as claimed in claim 1, wherein the controller is configured to determine one or more of a duration and an oxygen concentration for an oxygen supply interval by calculating a value for an internal circuit volume between the nebulizer and an end of the patient interface or coupler divided by the gas flow rate, to determine an amount of time required for an aerosol to be generated, transited through the flow line, and delivered at the patient interface.

8. The gas therapy system as claimed in claim 1, wherein the controller is configured to dynamically calculate aerosol generation and/or gas flow parameters dependent on location in the flow line of the nebulizer.

9. The gas therapy system as claimed in claim 1, wherein a concentration of the oxygen supplied from the gas source is modulated based on detected SpO2 levels.

10. The gas therapy system as claimed in claim 1, wherein the controller is configured to provide aerosol delivery during only a sub-set of inhalation periods.

11. A gas therapy system comprising:
a flow line, a gas source or a link to a gas source, and a nebulizer or a link to a nebulizer for aerosol delivery, a patient interface or a coupler for connection to a patient interface; and
a controller configured to modulate gas flow and aerosol delivery in real time,
wherein the controller is configured to change the gas flow rate from the gas source between at least one upper level and at least one lower level, to dynamically stop or reduce aerosol delivery during gas flow at the upper level, and to dynamically activate or increase aerosol delivery during intervals of gas flow at the lower level, and
wherein the controller is configured to determine a duration of the intervals of gas flow at the lower level based on a time required for an aerosol to be generated, transited through the flow line, and delivered at the patient interface.

12. The gas therapy system as claimed in claim 11, wherein the controller is configured to change to the lower gas flow level in advance of commencement of inhalation, by a time Δ1, and wherein Δ1 has a value in the range of 0.01 seconds to 3.0 seconds.

13. The gas therapy system as claimed in claim 12, wherein the controller is configured to activate aerosol generation during said interval a time duration Δ2 after switching to the lower gas flow level, and wherein the time duration Δ2 has a value in the range of 0.01 seconds to 3.0 seconds; and wherein the controller is configured to de-activate the aerosol generation a time duration Δ3 before end of inhalation, and wherein the time duration Δ3 has a value in the range of 0.01 seconds to 3.0 seconds; and wherein the controller is configured to raise the gas flow rate to the upper level a time duration Δ4 after end of inhalation.

14. The gas therapy system as claimed in claim 13, wherein the system comprises a flow sensor in the flow line and the controller is configured to use output signals from the flow sensor to monitor gas flow from the gas source and to use said flow monitoring when controlling the gas flow rate.

15. The gas therapy system as claimed in claim 11, wherein the controller is further configured to determine the amount of time required for the aerosol to be generated, transited through the flow line, and delivered at the patient interface at least in part by calculating a value for an internal circuit volume between the nebulizer and an end of the patient interface or coupler divided by the gas flow rate.

16. The gas therapy system as claimed in claim 11, wherein the controller is further configured to determine an oxygen concentration of the gas flow for the intervals based on the time required for the aerosol to be generated, transited through the flow line, and delivered at the patient interface.

17. A method of operation of a controller of a gas therapy system comprising a flow line, a gas source or a link to a gas source, and a nebulizer or a link to a nebulizer for aerosol delivery, and a patient interface or a coupler for connection to a patient interface, the method comprising:
modulating gas flow and aerosol delivery at intervals in real time, in which the controller changes a gas flow rate from the gas source between at least one upper level and at least one lower level to control a delivery of oxygen, and dynamically activates or increases aerosol delivery from the nebulizer based on a detection of inhalation,
wherein the controller is configured to perform modulation of a concentration of oxygen supplied from the gas source during the intervals based on changes in the gas flow rate.

18. The method of claim 17, further comprising:
dynamically stopping or decreasing aerosol delivery from the nebulizer based on a detection of exhalation.

19. The method of claim 18, wherein the controller switches between said levels in each of a succession of cycles, in which each cycle has specific upper and lower gas flow rate levels; and wherein said cycles have a duration in a range of 1 second to 2 hours.

20. The method of claim 19, further wherein inhalation is detected using a pressure or humidity sensor.

* * * * *